US008075509B2

(12) United States Patent
Molducci et al.

(10) Patent No.: US 8,075,509 B2
(45) Date of Patent: Dec. 13, 2011

(54) MEDICAL APPARATUS

(75) Inventors: Fabrizio Molducci, San Felice sul Panaro (IT); Fabio Roncadi, Mirandola (IT); Paolo Rovatti, Finale Emilia (IT)

(73) Assignee: Gambro Lundia AB, Lund (SE)

( * ) Notice: Subject to any disclaimer, the term of this patent is extended or adjusted under 35 U.S.C. 154(b) by 688 days.

(21) Appl. No.: 12/064,401

(22) PCT Filed: Aug. 25, 2005

(86) PCT No.: PCT/IB2005/002515
§ 371 (c)(1),
(2), (4) Date: Feb. 21, 2008

(87) PCT Pub. No.: WO2007/023328
PCT Pub. Date: Mar. 1, 2007

(65) Prior Publication Data
US 2008/0249377 A1    Oct. 9, 2008

(51) Int. Cl.
*A61M 37/00* (2006.01)
*C02F 1/44* (2006.01)

(52) U.S. Cl. ............. 604/6.09; 604/4.01; 604/5.01; 604/5.04; 604/6.1; 604/6.11; 210/645; 210/646

(58) Field of Classification Search ............ 604/4.01, 604/5.01, 5.04, 6.09, 6.1, 6.11; 210/645, 210/646
See application file for complete search history.

(56) References Cited

U.S. PATENT DOCUMENTS

| 4,990,258 | A | 2/1991 | Bjare et al. |
| 5,247,434 | A | 9/1993 | Peterson et al. |
| 5,326,476 | A | 7/1994 | Grogan et al. |
| 5,486,286 | A | 1/1996 | Peterson et al. |
| 5,487,827 | A | 1/1996 | Peterson et al. |
| 5,546,582 | A | 8/1996 | Brockmeyer et al. |
| 5,581,687 | A | 12/1996 | Lyle et al. |
| 5,656,153 | A | 8/1997 | Kameno et al. |
| 5,788,851 | A | 8/1998 | Kenley et al. |
| 5,858,239 | A | 1/1999 | Kenley et al. |
| 5,903,211 | A | 5/1999 | Flego et al. |
| 5,956,023 | A | 9/1999 | Lyle et al. |
| 6,143,181 | A | 11/2000 | Falkvall et al. |
| 6,144,837 | A | 11/2000 | Quy |
| 6,146,523 | A | 11/2000 | Kenley et al. |
| 6,256,643 | B1 | 7/2001 | Cork et al. |
| 6,284,131 | B1 | 9/2001 | Hogard et al. |
| 6,363,290 | B1 | 3/2002 | Lyle et al. |
| 6,468,241 | B1 | 10/2002 | Gelfand et al. |

(Continued)

FOREIGN PATENT DOCUMENTS

DE    197 42 633 A1    4/1999

(Continued)

*Primary Examiner* — Leslie Deak
(74) *Attorney, Agent, or Firm* — Pearne & Gordon LLP (57) ABSTRACT

A medical apparatus (1) comprises a user interface (30), a number of sensors (16,27,21,22,29) and a control system (18) programmed for displaying on the user interface screen (31) a number of indicia (37), each relating to a corresponding parameter and comprising an indicium border (45) delimiting an indicium selection area (45*a*); the control system allows selection of an indicium for identifying the parameter a user intends to modify, allows setting of a new set value for the selected parameter; the control system also receives from the sensors (29) a measure of the actual value for the parameter and displays on the indicium selection area (45*a*) of the indicium both the actual value and the set value for the same parameter. The programming software for the control system is also disclosed.

28 Claims, 5 Drawing Sheets

U.S. PATENT DOCUMENTS

| | | |
|---|---|---|
| 6,542,910 B2 | 4/2003 | Cork et al. |
| 6,610,024 B1 | 8/2003 | Benatti |
| 6,685,664 B2 | 2/2004 | Levin et al. |
| 6,695,806 B2 | 2/2004 | Gelfand et al. |
| 6,738,052 B1 | 5/2004 | Manke et al. |
| 6,773,412 B2 | 8/2004 | O'Mahony et al. |
| 6,775,577 B2 | 8/2004 | Crnkovich et al. |
| 6,811,707 B2 | 11/2004 | Rovatti et al. |
| 2002/0151804 A1 | 10/2002 | O'Mahony et al. |
| 2003/0152482 A1 | 8/2003 | O'Mahony et al. |
| 2003/0218623 A1 | 11/2003 | Krensky et al. |
| 2004/0084358 A1 | 5/2004 | O'Mahony et al. |

FOREIGN PATENT DOCUMENTS

| | | |
|---|---|---|
| DE | 100 13 666 A1 | 10/2001 |
| EP | 0 432 138 A1 | 6/1991 |
| EP | 0 686 404 A1 | 12/1995 |
| EP | 0 901 798 A1 | 3/1999 |
| WO | WO 96/13216 A1 | 5/1996 |

MEDICAL APPARATUS

TECHNICAL FIELD

The invention relates to a medical apparatus having an improved user interface. The medical apparatus of the invention could be an apparatus intended for the extracorporeal treatment of blood, for instance by hemodialysis, hemofiltration, hemodialfitration, ultrafiltration, plasmapheresis or an apparatus for processing whole blood and/or blood components.

BACKGROUND ART

Blood treatment apparatus and similar medical devices comprise an extracorporeal circuit, provided with at least one blood treatment or blood processing unit, one tube, connecting a blood removal zone to said unit, and a second tube, extending downstream of the treatment or processing unit towards a blood return zone to the patient or towards a blood/blood components collection zone. Blood is moved from the patient or donor to the treatment or processing unit via pumps or other actuators controlled by the machine.

In case the machine is for instance a hemodialysis apparatus, then for achieving the required treatment of blood, an adequately prepared dialysis liquid shall be sent to the treatment unit, and water removal through the treatment unit membrane as well other machine parameters shall be controlled. Depending upon the type of hemodialysis machine and upon the type of treatment, a user can have the possibility to set a number of parameters in order to impose a specific prescription to a patient, such as for instance: flow rates of the various liquids, temperatures and conductivity of the liquids, concentration of the liquids used during treatment, flow rates of any anticoagulants used and delivered during treatment, pressures in the fluid conduits, net liquid removal rates of plasma water from whole blood and so on.

It is therefore evident that users (the patient himself, a physician, a nurse) have normally a plurality of parameters to set before or even during the process performed by the medical apparatus.

In this situation easy and safe data entry as well as reliable data storage and transmission are particularly important in machines as blood treatment machines or blood processing apparatus where the process executed by the machine acts on a patient's or donor's blood. Particularly, in case of treatment of patients suffering from kidney failure, the patient is constantly connected to the machine with the serious risk that any failure in entering or in actuating a prescription could have negative impacts on the treatment delivery and on patient's health.

It is also to be noted that when setting up a blood treatment machine or similar apparatus, the user has to enter a relatively big number of treatment parameters and of machine operation parameters. This is accomplished giving the user possibility of navigation through various data entry screens wherein parameters of the same typology or parameters referring to a common context can be entered.

In this situation several technical solutions have been developed in the past in order to render parameters values data entry in blood treatment or blood processing apparatus relatively easy and reliable.

A data entry user interface of general purpose and not specifically designed for the medical field is known from U.S. Pat. No. 5,546,582.

A first known method for entering data in a dialysis machine is described in U.S. Pat. No. 5,247,434. This method comprises the following steps:
(a) providing a touch screen interface with an indicium thereon corresponding to a treatment parameter;
(b) touching the indicium;
(c) in response to said touching, invoking a data entry pad on a region of the touch screen;
(d) entering a parametric value corresponding to the treatment parameter by touching one or more buttons of the data entry pad;
(e) touching a first region of the data entry pad to signal entry of the parametric value;
(f) displaying on the touch screen a button soliciting verification of the newly entered parametric value;
(g) touching the button soliciting verification; and
(h) in response to steps (b)-(g), causing the parametric value corresponding to the treatment parameter to be changed.

In other words before really implementing a change a user is solicited to verify the newly entered parameter and to press a button confirming the change.

The same patent also discloses a method for entering variable parameters, i.e. parameters that can vary in the course of time during treatment.

More in detail U.S. Pat. No. 5,247,434 shows a method of programming a time-varying parameter comprising the steps:
(a) providing a touch screen interface;
(b) displaying on the touch screen first and second axes, the first axis corresponding to the time-varying parameter, the second axis corresponding to time;
(c) touching the touch screen at a plurality of points to define points on a parameter-versus-time curve;
(d) presenting on the touch screen a series of bars corresponding to said curve;
(e) selecting one of said bars for alteration;
(f) displaying on the screen a numeric parameter corresponding to the selected bar;
(g) touching the screen at first or second locations to increase or decrease, respectively, the displayed numeric parameter and thereby alter the value of the numeric parameter to which the selected bar corresponds;
(h) touching the screen at a third location to signify completion of steps (b)-(g); and
(i) storing data corresponding to the bars in a memory to which the process-control system can refer in changing the time-varying parameter with time.

Document U.S. Pat. No. 5,326,476 teaches a further method for entering a time variable parameter, ultrafiltration in particular, in a hemodialysis machine, having a programmable memory and having ultrafiltration capability, so as to enable the machine to perform ultrafiltration of fluid from a patient according to a time-variable ultrafiltration profile. The method disclosed in U.S. Pat. No. 5,326,476 comprises the following steps:
 (a) entering into the programmable memory a prescribed time for dialysis;
 (b) entering into the programmable memory a target ultrafiltration volume of fluid to be removed from the patient;
 (c) entering into the programmable memory a proposed ultrafiltration profile being representable as a plot of coordinates on an ultrafiltration rate axis and a time axis and defining a profile ultrafiltration volume; and
 (d) shifting the proposed ultrafiltration profile along the ultrafiltration rate axis to the degree necessary to make the profile ultrafiltration volume equal to the target ultrafiltration volume, so as to allow the hemodialysis machine to achieve, while ultrafiltrating the fluid according to the shifted ultrafiltration profile, the entered target ultrafiltration volume within the entered prescribed time.

This method allows the user to enter a profile curve and to move the ultrafiltration profile along the ordinates so as to achieve the desired integral value in the desired time frame.

A further user interface system for a dialysis machine is known from document U.S. Pat. No. 5,788,851 and comprises:

- a touch screen displaying messages and information and permitting to select a parametric value pertinent to operation of said machine or pertinent to a treatment by said machine,
- one hard key off of said touch screen, said touch screen prompting a user to press said hard key to signify that the selection of the parametric value has been completed;
- a control system having a host and a safety processing unit, wherein pressing of said hard key causes transfer of information relating to the selected parametric value from the host processing unit to the safety processing unit which is then checking said selected parametric value to confirm that said parametric value meets validation or safety criteria for a patient connected to said machine.

The above system is therefore using two processing units to avoid that unsafe parameters values are entered into the machine.

It is also known from U.S. Pat. No. 6,811,707 using a dialysis machine wherein after entry of a value for a parameter the value is stored in at least two different memory locations connected to corresponding separate main control units. At predetermined intervals of time, one of the units sends the dialysis treatment parameters values stored in its memory to the other unit. The values are then compared and an alarm signal generated if the values of the same parameters in the two memories of the two units do not coincide with each other.

Finally it is known to adopt on dialysis machines a visualization of both the value set by the user for a parameter and the value actually achieved by the machine for the same parameter. This double visualization is however done in a way such that the user has to navigate through several menus or displays of the user interface to have access to both the set information and the actually measured parameter value.

SUMMARY OF THE INVENTION

While the above disclosed systems and methods served to give the user possibility to enter data in a relatively easy manner and/or served to reduce data entry errors or data memorization errors, the present invention aims to further improve ease and reliability in data entry and visualization procedures for medical devices and particularly for blood treatment or blood processing machines.

In particular the invention aims to reduce as possible the efforts for the user to retrieve and have visualized key information during data entry procedures and/or during treatment. Furthermore the invention aims to offer the user immediate perception of the effect of parameter settings modification.

The above aims are reached by a medical apparatus and according to the appended claims. Further characteristics and advantages will better emerge from the following description in relation to some preferred but non-exclusive embodiments of an apparatus according to the invention.

SHORT DESCRIPTION OF THE DRAWINGS

The description will be made with reference to the figures of the accompanying drawings, provided by way of non-limiting example, in which.

DETAILED DESCRIPTION

With reference to the figures, reference number 1 denotes a medical apparatus. The medical apparatus of the shown embodiment is a machine for the extracorporeal treatment of blood. Of course the medical apparatus of the invention could alternatively be a blood processing device or a blood component preparation device or other medical apparatus for fluid delivery/collection.

Figure 1:
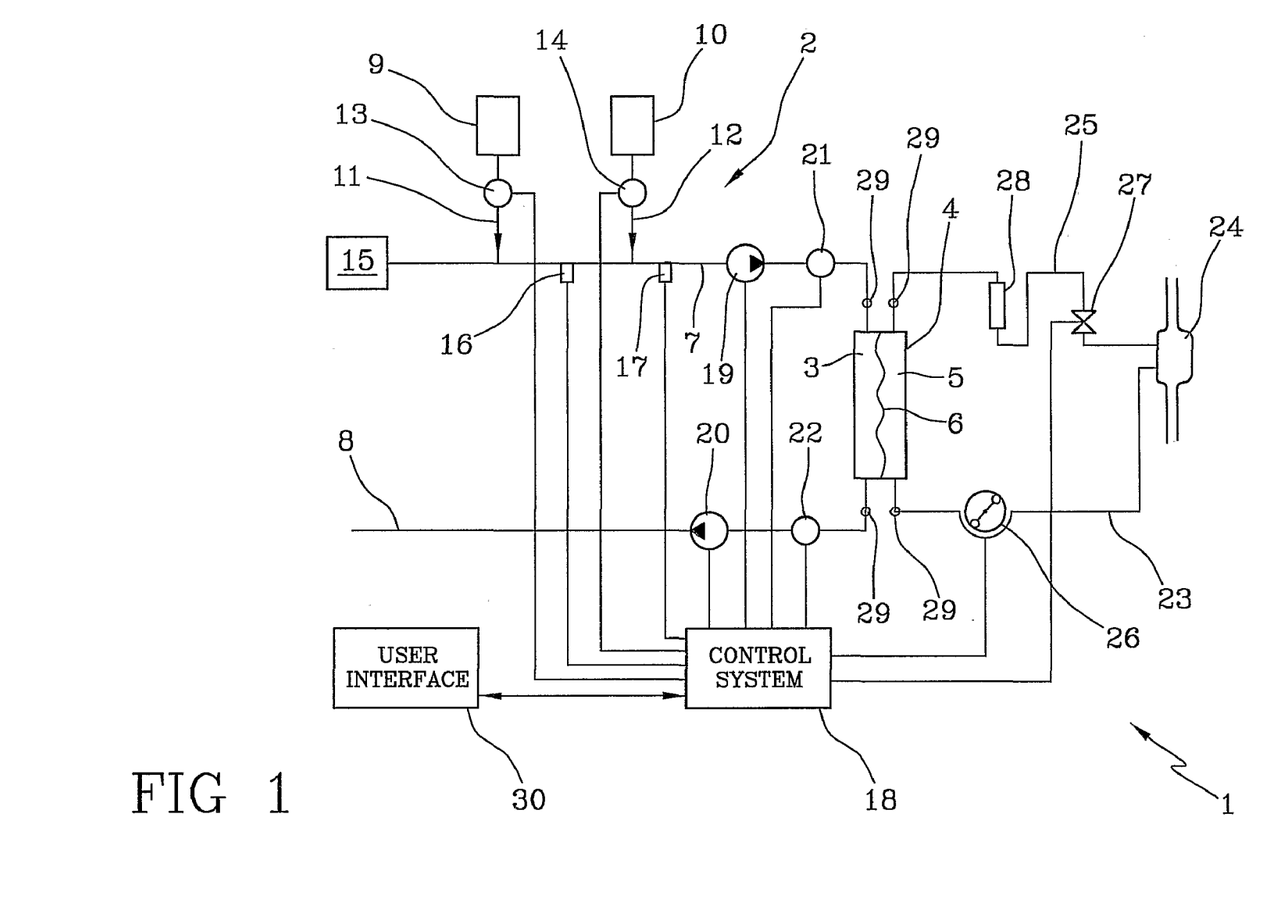
FIG. 1 is a schematic representation of a medical apparatus, for instance a blood treatment machine, according to the invention.

The apparatus shown in the enclosed drawings comprises a module 2 for preparing dialysis liquid to be sent into a first chamber 3 of a blood treatment unit 4, which is formed by a casing defining at least two chambers 3, 5 separated by a semipermeable membrane 6. The dialysis preparation module 2 includes tubing 7 bringing dialysis liquid to the first chamber inlet, while a waste line 8 receives spent liquid exiting via an outlet of the first chamber. In detail, the module 2 includes one or more concentrate containers 9, 10 delivering concentrated solutions, via respective lines 11, 12 and upon the action of respective concentrate pumps 13, 14, into the tubing 7 thereby properly mixing water coming from a source 15 with said concentrates and obtaining the dialysis liquid. Conductivity or concentration sensors 16, 17 can be provided on tubing 7 downstream each respective concentrate line. Said sensors provide control signals to a control system 18 which is responsible to then act on the concentrate pumps. Notice that sensors (not shown) detecting conductivity or concentration of electrolytes can also be present on the return tubing 8 containing waste liquid. A pump 19 is generally operating on tubing 7 and a pump 20 on the waste line 8. Of course different alternative embodiments can be envisaged to bring dialysis liquid to the treatment unit with appropriate chemical and physical properties. For instance pre-prepared dialysis liquid bags could be used with no need of online preparation of dialysis liquid starting from concentrates and water. Fluid balance sensors, for instance a first and a second flow-meter 21, 22, operating on tubing 7 and on waste line 8 respectively, are used and are connected to the control system to provide signals necessary for regulating at least one of pumps 19, 20. Of course other fluid balance systems can be used: scales for instance or balance chambers.

When the apparatus is in use, an extracorporeal blood circuit is connected to the second chamber 5. The extracorporeal circuit usually comprises at least an access branch 23 extending between a blood removal zone 24 from a patient or donor and the treatment unit 4, at least a return branch 25 extending downstream of the treatment unit, between the second chamber and a return zone of the blood to the patient; a peristaltic pump 26 is operatively associated to a length of pump tube of the extracorporeal circuit access branch. A clamp or other closure device 27 can operate on the blood return branch 25, typically downstream from a gas separator 28.

Usually, at the removal and return branches of the blood to or from the patient, access means are provided to the cardiovascular system of the patient, for example constituted by needles of appropriate sizes, catheters or accesses of different types. One or more liquid infusion lines could be provided connected at one end to an infusion liquid source (a bag or in-line infusion liquid preparation system) and at the other end to the extracorporeal circuit, or directly to the patient or donor.

Other sensors, such as pressure sensors 29, can be provided either on the extracorporeal circuit and/or on the dialysis liquid side of the apparatus. Furthermore sensors not herein disclosed in detail are provided with for directly or indirectly detecting the actual value of each machine or treatment parameter of interest, included those that can be set by the user, as it will appear from the following description.

The medical apparatus 1 can of course include other components, which are not herein disclosed, as they are not relevant for the purpose of the present invention.

User Interface

The apparatus 1 presents at least a user interface 30 for enabling setting of a plurality of parameters pertinent to operation of said apparatus or pertinent to a treatment to be performed by said apparatus. The parameters pertinent to the apparatus operation can be settings for one or more actuators (pumps, warmers, valves, etcetera depending upon the apparatus), while the parameters relating to the treatment performed by the apparatus can be settings on prescription parameters that have to be achieved (in case of blood treatment these settings can be fluid removal rate, total weight loss, concentration of substance in blood etcetera).

While the user interface herein disclosed is connected with and part of the apparatus 1, it shall be understood that the user interface 30 could be manufactured and sold separately and then connected to a medical apparatus. The user interface 30 of the embodiment shown includes a screen 31, for instance a touch screen, which allows interaction with the user interface, for instance selection of certain parameters, visualization, either in analogical or in digital form, of values of said parameters and display of other information as it will be here below in detail described.

The activity of the user interface is determined by control system 18, which is connected to the user interface, is responsive to actions by a user on said user interface, and controls operations of the medical apparatus 1 by acting on a plurality of actuators (such as pumps 12, 13, 19, 20, 27, valve 27 and others) and by receiving signals by a plurality of sensors (such as for instance sensors 12, 13, 21, 22, 29 etc.).

The control system of the presently shown embodiment includes a main control unit, connected to the user interface 30, and at least a memory connected to the main control unit. From a technical point of view the main control unit includes at least a microprocessor, while the above-mentioned memory can be in a single physical memory or in physically separated memory devices.

For the purpose of practically explaining the present invention, a non-limiting example of a possible implementation of the features of the present invention is given here below with reference to an embodiment of a user interface. Of course the present invention features could be applied to user interfaces other than the one disclosed herein in detail.

The control system 18 is programmed (for instance by loading a program in the memory which then is executed by the CPU) for carrying out the following steps, which serve to define the operating structure and logic of the user interface 30 shown in the attached figures.

Figure 2:
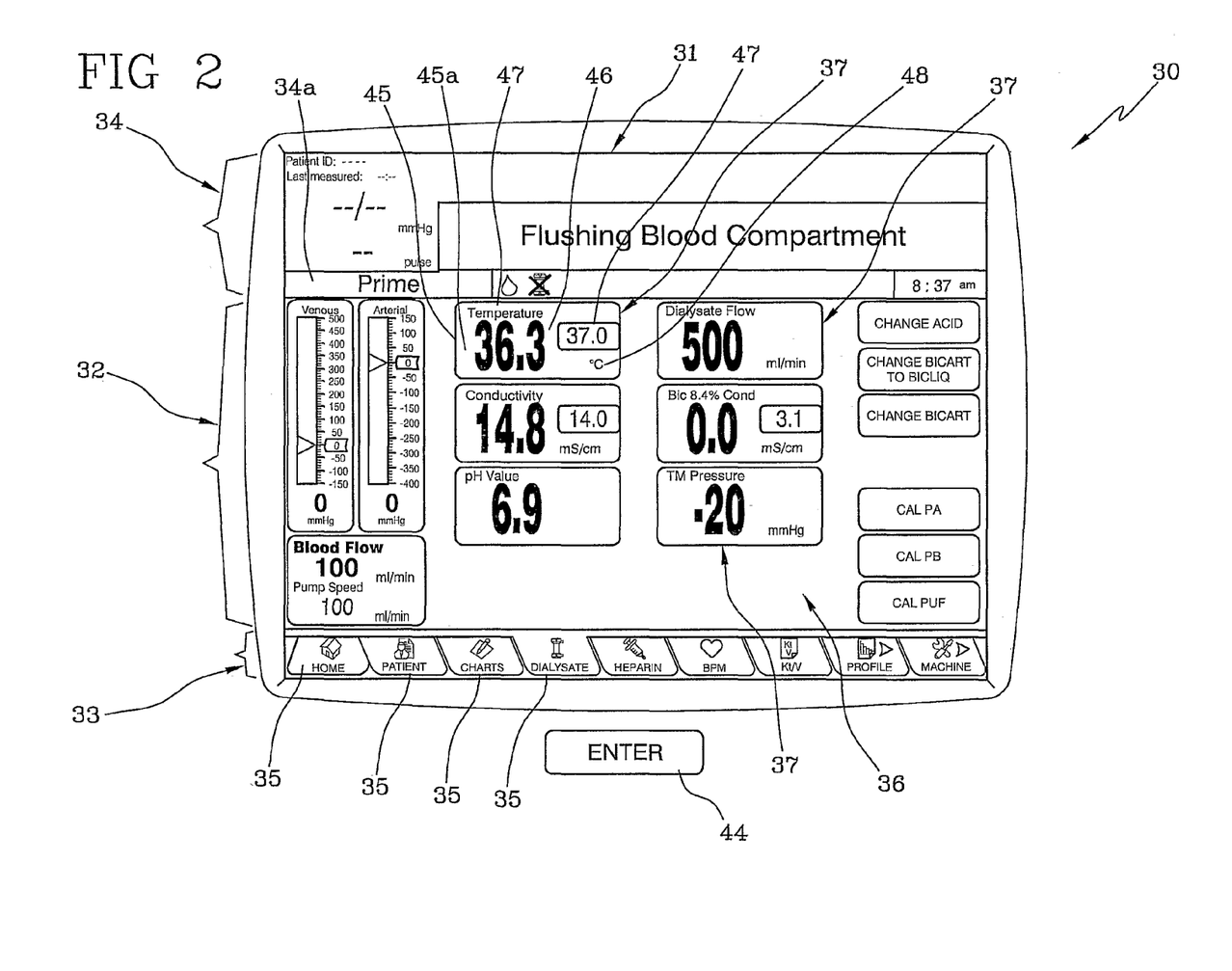
FIGS. 2 to 4 show a user interface of the apparatus of the invention in different operating moments.

According to the embodiment shown in the drawings, the control system defines on screen 31 an operating region 32, where a number of working displays can be displayed, and a navigation region 33, where a number of navigation keys can be displayed (see FIG. 2). The working displays are shown one per time according to a sequence, which depends upon the sequence of activation of the navigation keys, as it will be apparent from below description.

The operating region 32 of the embodiment in FIG. 2 is adjacent to and in contact with the navigation region 33 and, in particular, is placed between the navigation region and a status bar region 34 extending transversally in the top part of the screen 31.

The navigation region of the non-limitative embodiments shown is in the bottom part of the screen and contains a plurality of navigation keys 35.

Of course the relative positions of regions 32, 33 and 34 could be differently arranged without departing from the scope of the invention. The control system displays in the working region a plurality of working displays 36, each including one or more indicia, such as touch buttons or touch icons 37, which can be selected to access particular submenus and/or for selecting a parameter or a group of parameters for successive modification of the value(s) thereof.

Since the medical apparatus can be in different operating modes, for instance by way of non-limiting example idle mode, setup mode, priming mode, treatment (or dialysis) mode, and rinse-back mode, the user interface reflects said operating modes in the status region 34. This latter identifies, in a band 34*a*, information relating to the operating mode, while the working region shows a plurality of working displays accessible to the user for entering commands or for modifying settings of one or more parameters (see FIGS. 2 and 3). Each working display 36 can also display information, in alphanumeric or in analogical or in graphic form, regarding the status of the machine, its operating conditions, the current actual values of one or more parameters, etcetera. When displayed according to the technique here below described, each working display occupies the entire operating region, overlapping to or hiding previously displayed working displays. The status bar in addition to information concerning the status mode of the machine (flushing, treatment, priming, rinse back, etc.) or can also provide alarm or information messages 34*b* (see FIG. 2).

The control system is programmed to associate to each of said number of navigation keys 35 a corresponding working display 36 so that each working display is selectable and displayable in the working region upon selection of the corresponding navigation key. In other words the control system links the navigation key to one corresponding working display and therefore loads from a memory and displays on the operating region 32 of the screen the working display 36 associated to the navigation key selected by the user. Moreover the control system organizes a plurality of navigation keys (which are tab shaped in the non-limiting embodiments of the attached figures) and corresponding working displays according to a multi-level hierarchical organization where one root is present an where, upon selection of the navigation keys, it is possible for the user to access the several branches and sub-branches deriving from the root.

Figure 3:
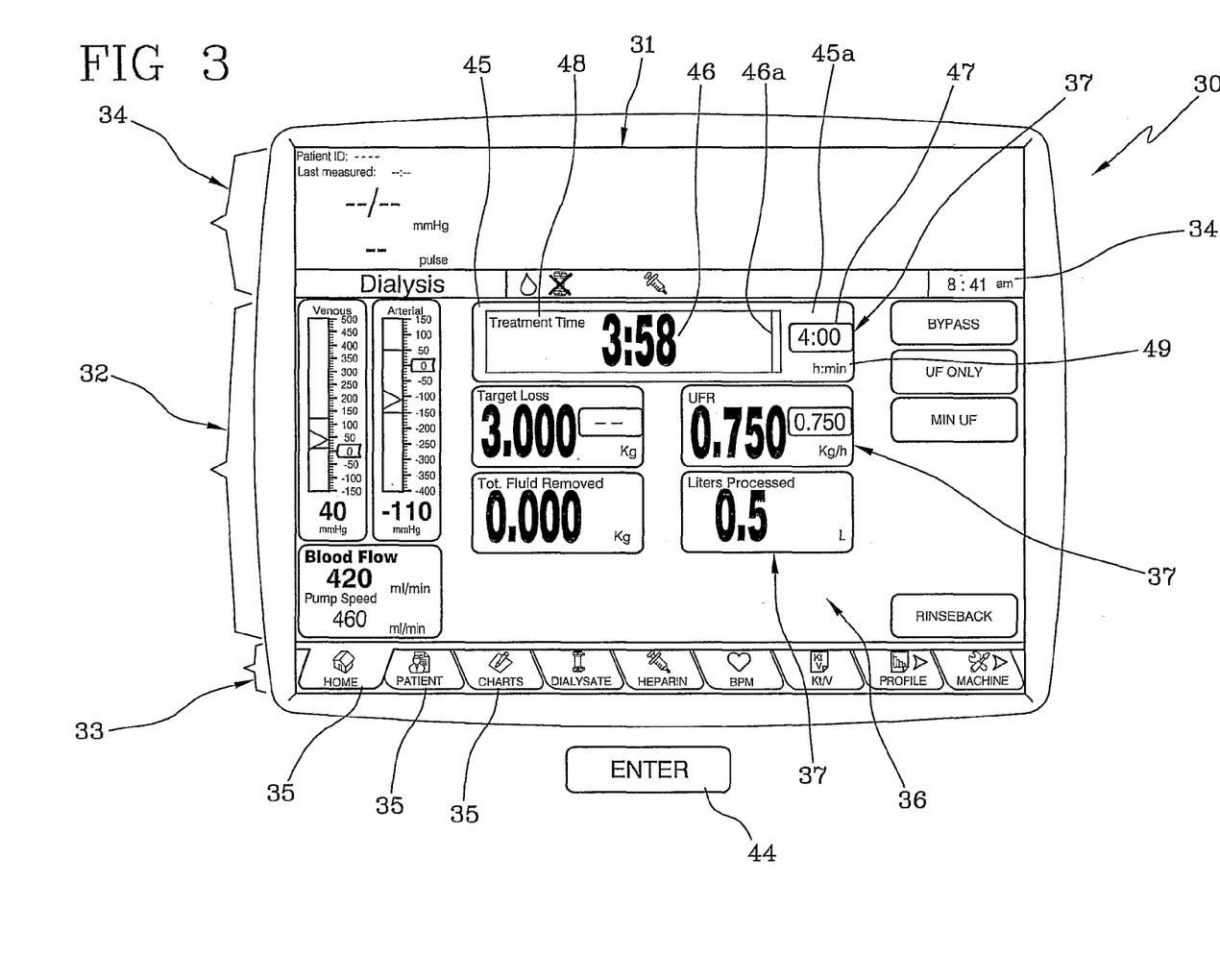

Again, while the above disclosed description refers to the user interface of the enclosed FIGS. 2 and 3 this shall not be interpreted as a limiting factor: indeed, the key features of the present invention could be applied to user interfaces having a navigation criteria and/or position and/or working of the graphic components displayed on screen different than the ones above disclosed.

As already mentioned, in the embodiment herein described the screen is a touch screen including said operating, said status, and said navigation regions; in this case the control unit allows selection of a key by detecting a touching of the corresponding area delimited by the key in the navigation region. Other techniques for key selection could be possible, for instance adopting a mouse or a stick cooperating with a pointer on screen.

As mentioned, when one key is selected at least one of said working displays is invoked on screen showing one or more indicia for identifying a parameter a user intends to modify. In FIG. 2 for instance, selection of the 'dialysate' tab key causes invocation of the working display 36, which includes a plurality of indicia 37 such as one for selection of dialysis liquid temperature, one for selecting dialysis liquid conductivity etcetera, one for dialysis liquid flow rate etcetera.

The control system is programmed for detecting touching of indicium 37. Touching of the indicium signifies selection of the indicium, identifies the parameter a user intends to modify (for instance in FIG. 4 the indicium 37 for modifying the target weight loss is selected and this means the user is then allowed to modify the target weight loss value), and allows setting of a new value for said parameter. Notice that in case a user interface with no touch screen is used, indicia selection can be carried out by alternative means: for instance by using an hardware pointing device (mouse, or stick, or keys) cooperating with a movable indicator on screen, or a keyboard allowing scrolling of a window or of some visually emphasizing means on screen, etcetera.

On the other hand, in case the user interface includes a touch screen, touch sensitive indicia 37 are defined on the touch screen for each parameter the user is allowed to select and modify in term of value (liquid temperatures, flows etc.). Each touch sensitive indicium, such as a touch sensitive button, comprises a border 45 delimiting the indicium selection area which is a touch sensitive area 45a; the border can be constituted, by a line (continuous or not) or simply by any visually differentiated representation of the indicium selection area 45a as compared to the background constituted by the working display 36 (for instance obtained by changing colour, tonality, or using appropriate texturing and/or rendering differentiating the selection area). In the embodiments shown where a touch screen based user interface is adopted, when the selection area 45a is touched, the indicium moves from a first to a second condition visually differentiated from the first condition. For instance in the second condition the indicium appears depressed and/or differently coloured or differently represented as compared to the first condition.

In the embodiment shown, in response to the touching of the indicium, the control system invokes a data-entry display 42 on the touch screen having at least two set buttons 43 such as buttons for each digit and-or buttons for increasing or decreasing the current value of the selected parameter. The display 42 could include an enter key 44 for entering the selected value. In other words the enter key can be either a touch sensitive area of the data entry display 42 or of the rest of the touch screen or a hard key off the touch screen (as in the enclosed figures). Once the new value has been set and entered, said new value is stored in a memory and represents the value desired by the user for a certain parameter. Alternatively to what above described the setting of a new value can be done as follows. The parameter is selected by a touching of indicium 37 on the active working display, and then in response to said touching, at least two set buttons and an enter key are activated on the touch screen working display (these keys could also be always available and active if enough room is available on the working display); then the user interface is controlled so that setting a of a new parametric value corresponding to the treatment parameter is obtained by touching one or more times the mentioned buttons (which can be shaped as arrow keys or + and − keys) and by detecting the touching of said enter key for signifying setting has been completed.

Of course other alternative method and means could be provided for data entry of new settings.

Referring to the embodiments shown, the interface 30 is associated to the extracorporeal blood treatment apparatus 1 and the parameters that can be selected and modified are one or more selected in the group comprising:
Temperature of the dialysis liquid,
Conductivity of the dialysis liquid,
Electrolytes concentration of the dialysis liquid,
Flow rate of the dialysis liquid,
Flow rate of the spent dialysate,
Flow rate of the blood in the in one of said tubing,
Ultrafiltration rate through the semipermeable membrane,
Net patient weight loss rate,
Treatment time,
Net weight loss,
Anticoagulant delivery rate and mode,
Infusion rate of substitution solution,
Infusion volume of substitution solution.

The plurality of parameters which can be set by the user through the user interface include a sub-group of parameters which are displayed as follows. This subgroup of parameters include one or more of the following parameters: treatment time (FIG. 3), total weight loss (target loss in FIG. 4) to be achieved during said treatment time, temperature of the dialysis liquid, conductivity of the fresh dialysis liquid (refer also to FIG. 2). These parameters are set by the user but the machine typically needs time to react to the user setting and, therefore, it is possible to have discrepancies or differences between the set value (i.e. the value entered by the user as desired value for a parameter) input by the user and the actual value actually present or achieved in a certain moment by the machine (that is the value actually achieved by the machine for a parameter, as measured by one or more sensors); notice that the actual value should tend to the set value and depending upon the tolerance ranges should more or less approach the value set by the user). This is very clear looking for instance to conductivity or temperature of the dialysis liquid (FIG. 2).

According to the invention, for those parameters of said subgroup, the current actual value and the set value of each one of the above parameters is displayed in same the selection area of the indicium 37 that the user shall touch or select to modify the set value of the same parameter.

In the embodiment shown the two values are contemporaneously displayed. This contemporaneous display can occur continuously (i.e. the control system is programmed to always display the two values) or only when the indicium is selected for modification.

Alternatively, the two values could be displayed in said selection area on different instants in time. For instance the control system can be programmed to display in the indicium selection area the actual value for the parameter, detect if a set value of a parameter is under modification, and then display in the indicium selection area (together with the actual value or not) the set value a user has set for the same parameter. Once the modification of the parameter has been completed (i.e. for instance when the machine detects that the enter key 44 has been pressed) the control system hides the display of the set value and displays again the actual value (or displays only the actual value, in case the two values where co-displayed during the set value modification) in said selection area.

Notice that the actual value and/or the set value can be displayed either in digital form (see FIG. 2) or in analogical form (see FIG. 3 where treatment time is expressed both in figures and by a bar 46a which decrements in length or size as treatment time progresses). Of course digital and analogical representation can be alternative or both present at the same time, as in FIG. 3 for treatment time. In any case both the set and the actual value of each of the parameters of said subgroup can be displayed in digital and/or analogical form on the same selection area of the indicium so that the user has perception of both values without need of any navigation through other working displays of the user interface.

According to the embodiment the touch sensitive area of the button includes two or more of the following display regions:

a first region 47 displaying the value a user has set for the parameter,     a second region 46 displaying the current actual value for the same parameter as measured by one or more sensors connected to the control unit of the machine 1 a third region 48 comprising an alphanumeric description of the parameter corresponding to the indicium, and     a fourth region 49 displaying a unit of measure of the value of the parameter.

In this way the user selects the parameter by touching the button, modifies the set value for the parameter, and has on the surface of the same button both visualization of the setting and of the current real value for the same parameter. This enhances usability as the operator has both displays in the region of his/her maximum attention, i.e. the touch sensitive area, which requires the touch to start the parameter value modification sequence. Moreover since the two values are contemporaneously and closely displayed the user has immediate feedback as to whether the machine reacts or not to the new setting with no need of any other navigation through the interface screens.

Figure 5:
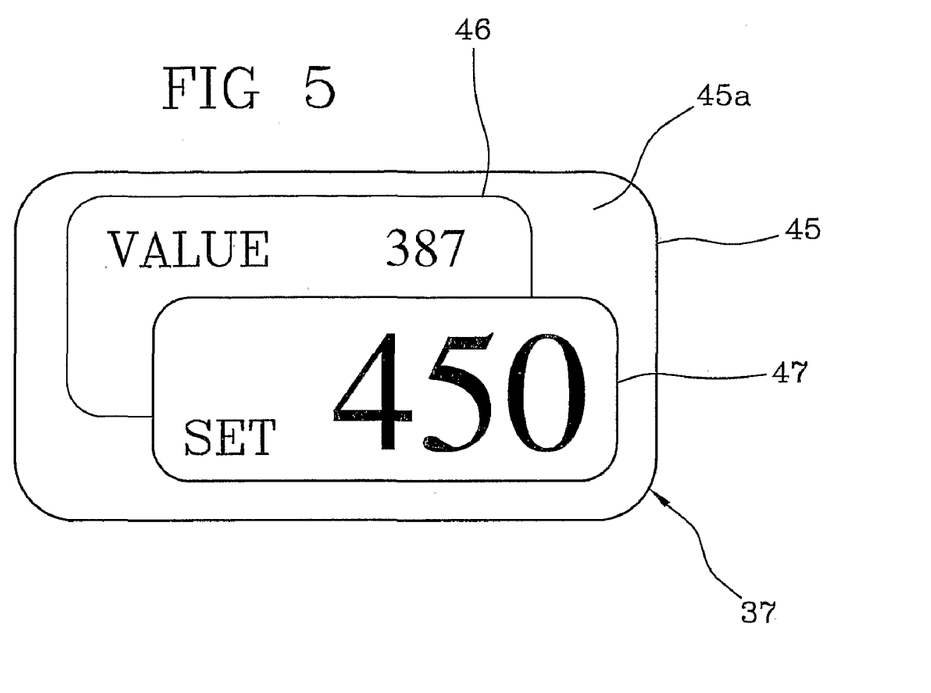
FIGS. 5 and 6 schematically show a detail of the user interface according to a possible variant of the invention.
Figure 6:
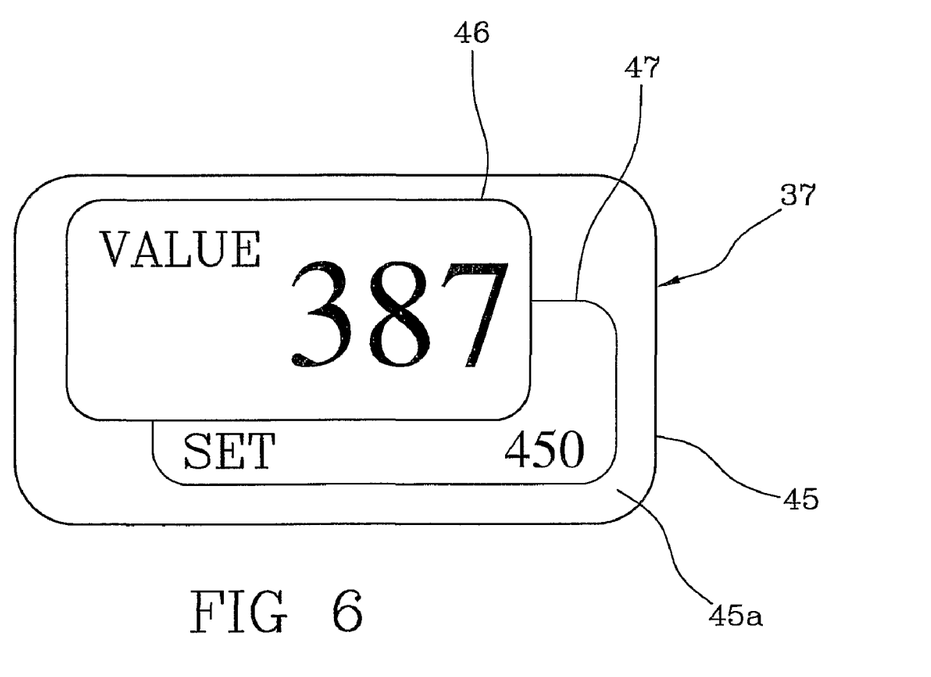

In FIGS. 5 and 6 a possible alternative of the above solution is disclosed. Indeed FIGS. 5 and 6 schematically show only the particular relating to an indicium 37, all remaining components of the interface remaining as already described.

The first region 47 of the indicium 37 displays the value a user has set for the parameter, and the second region 46 displays the current actual value for the same parameter as measured by one or more sensors connected to the control unit of the machine 1. However different from the first embodiment the two regions can be differently displayed the one from the other, depending upon the circumstances.

Indeed if the control system detects that a set value is under modification (for instance by detecting that the indicium has been selected, i.e. in case of touch screen based user interface by detecting that the indicium selection area 45a has been touched), then it controls the user interface to move the display of the first region (displaying the set value) from a first condition, of low graphical impact as in FIG. 6, to a second condition, of high graphical impact as in FIG. 5; vice-versa happens to the second region which is moved from a second condition of high impact as in FIG. 6, to a first condition, of low graphical impact as in FIG. 5.

Figure 4:
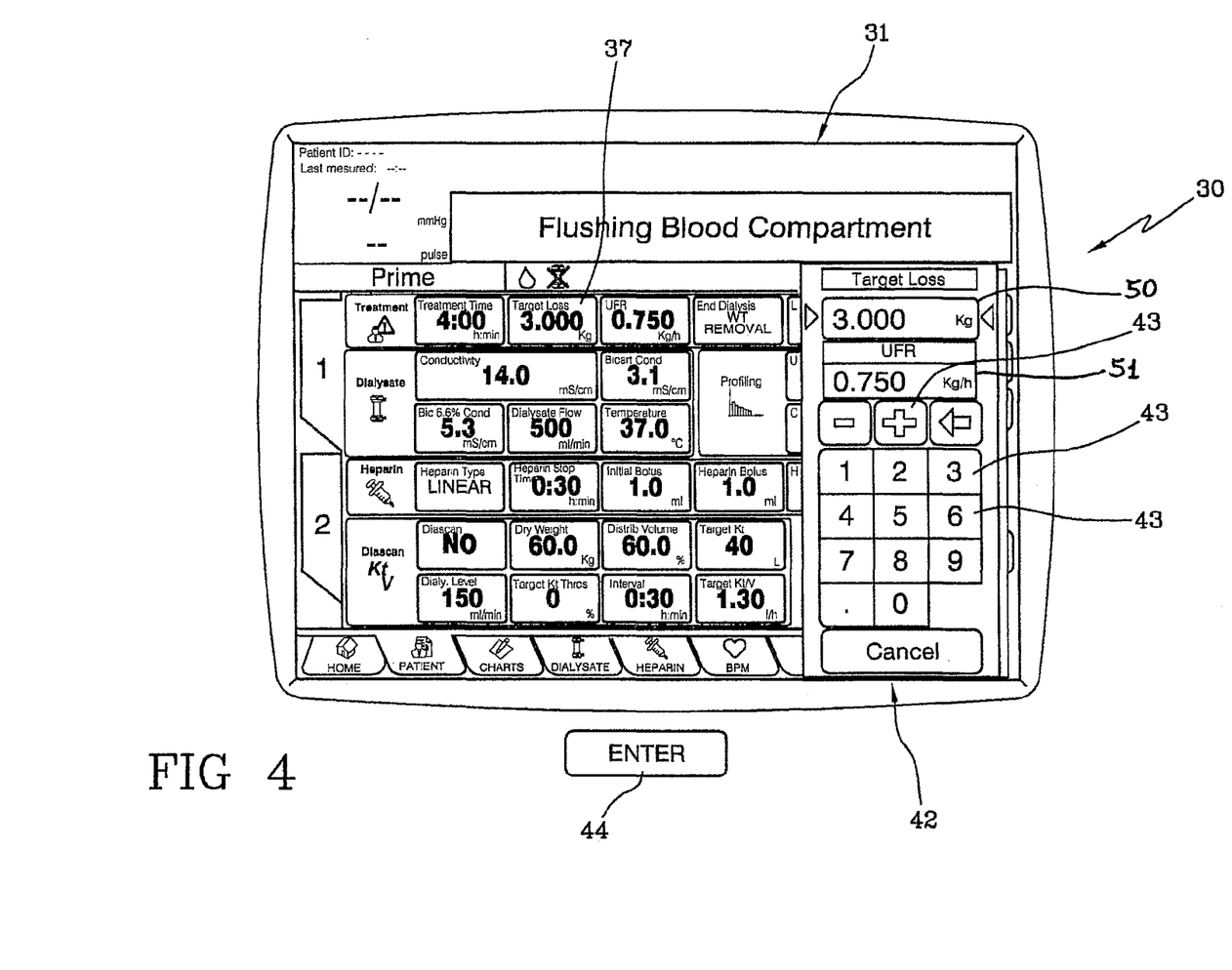

In addition, the control system can be also programmed to control the user interface to switch the first region from said second to said first display condition and to contemporaneously switch the second region from said first to said second display condition when at least one of the following conditions is met: either the control system receives from said sensors a new actual measured value of a parameter is under modification, or the control system recognizes that the parameter modification step has been completed (enter key 44 touched); or the control system recognizes that the parameter modification step has been cancelled (for instance by touching the key cancel on the data entry display 42—see FIG. 4).

The control system is programmed to differentiate display of the first and second regions when switching from said first to said second display conditions by one or more of the following:

differently colouring the area of the region when moving from the first to the second display condition,     differently rendering the area of the region when moving from the first to the second display condition,     differently texturing the area of the region when moving from the first to the second display condition,     resizing the dimension of the displayed value when moving from the first to the second display condition,     resizing the dimension of the region when moving from the first to the second display condition.

In the embodiment shown if FIGS. 5 and 6, to differentiate first and second conditions for the regions 46 and 47, the first condition of each region (low impact) is characterized by a relatively small area inside the indicium (as compared to the area dedicated to the same region when in the second condition), while the second condition (high impact) is characterized by a relatively big area inside the indicium (as compared to the area dedicated to the same region when in the first condition). In the embodiment of FIGS. 5 and 6, when moving from the first to the second condition the overall dimension of the displayed value is also resized. The first and second display conditions of the above two regions could also be differentiated by proper colouring or rendering or texturing, or by any other alternative graphic means.

According to a further aspect of the invention, which could be independently implemented or combined with the above disclosed features, the control system could be programmed to receive settings via the touch screen based user interface 30 for at least the following three parameters: net patient weight loss rate, treatment time, and patient weight loss. Then the control system detects a touching of said indicium selection area and invokes a data-entry display 42 on a region of the touch screen in response to said touching; according to this further aspect of the invention the data entry display comprises at least first 50 and a second display area 51 and the control system is programmed to detect if the set value of one of said three parameters is under modification and then calculate the set value of at least a second one of the other two of said three parameters as function of the value of the parameter under modification. Then the control system displays the set value of the parameter under modification in the first display area 50 and the set value of the second parameter in the second display area 51.

In particular if, as in FIG. 4, total patient weight loss (Target, loss in FIG. 4) is under modification, then the data entry, display 42 shows in the first display area 50 the new set value for the Target loss and in the second display area 51 the newly calculated set value for the net patient fluid removal rate (UFR in FIG. 4).

In other words when the user sets a new Total weight loss, since treatment time remains unchanged, then the control system recalculates, and advantageously shows to the user, the new value for the net fluid removal rate.

According to a further aspect the control system checks the compliance of both the new set value of the first parameter and the new calculated value of the second parameter with preset ranges. If following the new setting of the first parameter one or both the first and/or second parameter exit their respective ranges the control system visually informs the user about the out of range parameter on the data entry display, for instance by appropriately marking the display area. This is useful because it could happen that a user changes the total weight loss in a way that could be acceptable in term of weight loss only, but that would cause an excessive net fluid removal rate. Thanks to this aspect of the invention this is immediately evident to the user.

Software Program Product

The invention also concerns a software program comprising instructions which, when executed by the main control system of the apparatus 1 or of the user interface, programs the control system to execute the steps which have been already disclosed in the chapter 'user interface' and therefore not herein repeated. The software program can be stored in any adequate support and then sold separately from the medical apparatus 1. In practice the software program could be stored on a magnetic recording support (for instance an hard disk, a cassette, a floppy disk, etcetera), or on an optical recording support (DVD or CD or other), on an electrical or electromagnetic carrier signal (if for instance the program is sent via a network), or on a computer readable memory (ROM, EPROM, RAM), or other convenient support memory device and then associated to the machine control system which running the program stored on said support is then programmed to render available a user interface having the features above described.

The invention claimed is:

1. Medical apparatus comprising:
   at least a user interface for enabling setting of a plurality of parameters pertinent to operation of said apparatus or pertinent to a process to be performed by said apparatus, the user interface including at least a screen;
   a number of sensors for detecting actual values of said parameters;
   a control system for controlling operation of said medical apparatus, the control system being connected to said sensors, being responsive to actions by a user on said user interface, and being programmed for executing the following steps:
      displaying on said screen a number of indicia, each relating to a corresponding parameter and comprising an indicium border delimiting an indicium selection area;
      allowing selection of an indicium among said number for identifying the parameter a user intends to modify,
      allowing setting of a new set value for said parameter;
      receiving from at least one of the sensors a measure of the actual value for said parameter;
      displaying on the indicium selection area of the indicium both the actual value and the set value for the corresponding parameter,
   the control system being programmed to contemporaneously display in the indicium selection area of a same parameter the following regions:
      a first region displaying the set value a user has set for the parameter,
      a second region, distinct from the first region, displaying the current actual value for the same parameter,
      the first region and the second region occupying respective areas having different sizes on the indicium selection area.

2. Apparatus according to claim 1, wherein the control system is programmed to store in a memory the set value for each parameter and the measured value for the same parameter, the measured values being periodically updated and corresponding updated values displayed in the selection area of the corresponding indicium.

3. Apparatus according to claim 1, wherein the control system is programmed to display in the indicium selection area the actual value for the parameter and, on a different time instant, the set value a user has set for the parameter.

4. Apparatus according to claim 1, wherein the control system is programmed to:
   display in the indicium selection area the actual value for the parameter,
   detect if a set value of a parameter is under modification, and then
   display in the indicium selection area the set value a user has set for the same parameter.

5. Apparatus according to claim 4, wherein the control system is programmed to detect if a set value of a parameter is under modification by at least detecting if the corresponding indicium has been selected.

6. Apparatus according to claim 4, wherein the control system is programmed to control the user interface not to display in the indicium selection area the actual value of the parameter during the set value modification and to re-display the actual value when the set value modification has been completed.

7. Apparatus according to claim 1, wherein the control system is programmed to contemporaneously display in the indicium selection area the following further regions:
   a third region comprising an alphanumeric description of the parameter corresponding to the indicium, and
   a fourth region displaying a unit of measure of the value of the parameter.

8. Apparatus according to claim 1, wherein the control system is programmed to display the first region according to at least a respective first display condition and a respective second display condition visually differentiated from the first condition.

9. Apparatus according to claim 8, wherein the control system is programmed to display the second region according to at least a respective first display condition and according to a respective second display condition visually differentiated from the first condition.

10. Apparatus according to claim 9, wherein the control system is programmed to control the user interface to modify the first region from said second to said first display condition and to contemporaneously modify the second region from said first to said second display condition when at least one of the following conditions is met:
    either the control system receives from said sensors a new actual measured value of a parameter is under modification, or
    the control system recognizes that the parameter modification step has been completed; or
    the control system recognizes that the parameter modification step has been cancelled.

11. Apparatus according to claim 9, wherein the control system is programmed to differentiate visualization of the first and second regions when switching from said first to said second display conditions by one or more actions selected in the group comprising:
    differently colouring the area of the region when moving from the first to the second display condition,
    differently rendering the area of the region when moving from the first to the second display condition,
    differently texturing the area of the region when moving from the first to the second display condition,
    resizing the dimension of the displayed value when moving from the first to the second display condition,
    resizing the dimension of the region when moving from the first to the second display condition.

12. Apparatus according to claim 8, wherein the control system is programmed to detect if a set value of a parameter is under modification, and to then control the user interface to modify the first region from said first to said second display condition and to contemporaneously modify the second region from said second to said first display condition.

13. Apparatus according to claim 12, wherein the control system is programmed to detect if a set value of a parameter is under modification by at least detecting if the corresponding indicium has been selected.

14. Apparatus according to claim 8, wherein the control system is programmed to differentiate display of the first and second regions when switching from said first to said second display conditions by one or more actions selected in the group comprising:
   differently colouring the area of the region when moving from the first to the second display condition,
   differently rendering the area of the region when moving from the first to the second display condition,
   differently texturing the area of the region when moving from the first to the second display condition,
   resizing the dimension of the displayed value when moving from the first to the second display condition,
   resizing the dimension of the region when moving from the first to the second display condition.

15. Apparatus according to claim 1, wherein the screen comprises a touch screen, said indicium selection area delimited by the indicium border being touch sensitive.

16. Apparatus according to claim 15, wherein the step of allowing selection of the indicium comprises detecting touching said indicium selection area, said step of allowing setting of a parameter value comprises the step of invoking a data-entry display on the touch screen in response to said touching.

17. Apparatus according to claim 16, wherein said data entry display has at least two set buttons and an enter key and wherein said step of allowing setting of a parameter value further comprises the steps of:
   receiving a setting of a parametric value corresponding to the treatment parameter by touching one or more buttons of the data-entry display;
   detecting the touching of said enter key for signifying setting has been completed.

18. Apparatus according to claim 16, wherein:
   said data entry display has at least two set buttons and the user interface comprises at least an enter hard key off of said touch screen and connected to the control system, and wherein said step of allowing setting of a parameter value further comprises the steps of:
   receiving a setting of a parametric value corresponding to the treatment parameter by touching one or more buttons of the data-entry display;
   detecting the touching of said enter key for signifying setting has been completed.

19. Apparatus according to claim 16, wherein the data entry display comprises at least first and a second display area, the control system being programmed to:
   detecting if the set value of the parameter under modification is actually modified,
   calculating the set value of at least a second parameter which is function of the value of the parameter under modification,
   displaying the set value of the parameter under modification in the first display area;
   displaying in the second display area the calculated set value of the second parameter.

20. Apparatus according to claim 1, wherein the screen comprises a touch screen, said indicium selection area delimited by the indicium border being touch sensitive, and wherein said step of allowing selection of the indicium comprises detecting a touching of said indicium selection area,
said step of allowing setting of a parameter value comprises the following steps:
   in response to said touching, activating on the touch screen at least two set buttons and an enter key;
   receiving a setting a parametric value corresponding to the treatment parameter by touching one or more buttons;
   detecting the touching of said enter key for signifying setting has been completed.

21. Apparatus according to claim 1, comprising:
   a dialysis liquid preparation module for preparing dialysis liquid,
   at least a waste line for receiving spent dialysate,
   a blood removal tubing,
   a blood return tubing, and
   a blood treatment unit having a first chamber connected to dialysis liquid preparation module and to the waste line, and a second chamber connected to the blood removal and to the blood return tubing, said first and second chamber being separated by a semipermeable membrane.

22. Apparatus according to claim 21, wherein the control system is programmed to identify a sub-group of said parameters, said subgroup comprising one or more of the following:
   Temperature of the dialysis liquid,
   Conductivity of the dialysis liquid,
   Electrolytes concentration of the dialysis liquid,
   Flow rate of the dialysis liquid,
   Flow rate of the spent dialysate,
   Flow rate of the blood in the in one of said tubing,
   Ultrafiltration rate through the semipermeable membrane,
   Net weight loss rate,
   Treatment time,
   Weight loss.

23. Apparatus according to claim 22, wherein the control system is programmed for displaying, on the selection area of the indicium of each parameter in said subgroup, both the actual value and the set value for the corresponding parameter.

24. Apparatus according to claim 1, comprising:
   a dialysis liquid module for delivery of fresh dialysis liquid,
   at least a waste line for receiving spent dialysate,
   a blood removal tubing,
   a blood return tubing, and
   a blood treatment unit having a first chamber connected to dialysis liquid module and to the waste line, and a second chamber connected to the blood removal and to the blood return tubing, said first and second chamber being separated by a semipermeable membrane, wherein:
   the user interface screen comprises a touch screen, said indicium selection area delimited by the indicium border being touch sensitive,
   the control system is programmed to receive settings via the user interface for at least the following three parameters: net patient weight loss rate, treatment time, and total patient weight loss,
   the step of allowing selection of the indicium comprises detecting a touching said indicium selection area, the step of allowing setting of a parameter value comprises the step of invoking a data-entry display on the touch screen in response to said touching, the data entry display comprising at least first and a second display area, the control system being programmed to:
    detecting if the set value of one of said three parameters is under modification,
    calculating the set value of at least a second one of the other two of said three parameters as function of the value of the parameter under modification,
    display the set value of the parameter under modification in the first display area;
    display in the second display area the calculated set value of the second parameter.

25. Apparatus according to claim 24, wherein the first parameter is either treatment time or total patient weight loss, the second parameter is net patient weight loss rate and wherein the control system is programmed to check compliance of the values of said first and second parameters with respective ranges, visually signalling on the touch screen occurrence of any out of range situation.

26. Apparatus according to claim 1, wherein the control system is programmed to display the actual value on the indicium selection area either in digital or in analogical form.

27. Apparatus according to claim 1, wherein the control system is programmed to display the set value on the indicium selection area either in digital or in analogical form.

28. Software program stored on a support selected from the group consisting of a magnetic recording support, an optical recording support, a ROM memory and a RAM memory, wherein the program comprises instructions that, when executed, program the control system to execute the steps claimed in claim 1.

* * * * *